(12) United States Patent
Nakaji et al.

(10) Patent No.: US 8,939,881 B2
(45) Date of Patent: Jan. 27, 2015

(54) APPARATUS FOR LOADING DOSIMETRICALLY CUSTOMIZABLE BRACHYTHERAPY CARRIERS

(75) Inventors: Peter Nakaji, Phoenix, AZ (US); David Brachman, Phoenix, AZ (US); Heyoung McBride, Phoenix, AZ (US); Emad Youssef, Tempe, AZ (US); Theresa Thomas, Gilbert, AZ (US)

(73) Assignee: Gammatile LLC, Gilbert, AZ (US)

( * ) Notice: Subject to any disclaimer, the term of this patent is extended or adjusted under 35 U.S.C. 154(b) by 0 days.

(21) Appl. No.: 13/460,809

(22) Filed: Apr. 30, 2012

(65) Prior Publication Data
US 2013/0338423 A1 Dec. 19, 2013

Related U.S. Application Data

(60) Provisional application No. 61/480,304, filed on Apr. 28, 2011.

(51) Int. Cl.
*A61N 5/00* (2006.01)
*A61N 5/10* (2006.01)

(52) U.S. Cl.
CPC ............ *A61N 5/1007* (2013.01); *A61N 5/1027* (2013.01); *A61N 5/103* (2013.01); *A61N 5/1014* (2013.01); *A61N 2005/1023* (2013.01)

USPC ........ 600/8; 600/1; 600/7; 128/897; 128/898; 128/899

(58) Field of Classification Search
CPC .................... A61N 5/1027; A61N 2005/1023; A61N 5/1014; A61N 5/103; A61N 5/1007
USPC ............................... 600/1, 8, 7; 128/897–899
See application file for complete search history.

(56) References Cited

U.S. PATENT DOCUMENTS

| | | | |
|---|---|---|---|
| 5,967,966 A * | 10/1999 | Kronholz et al. | 600/3 |
| 2003/0130573 A1 * | 7/2003 | Yu et al. | 600/407 |
| 2004/0242953 A1 * | 12/2004 | Good | 600/7 |
| 2005/0035310 A1 * | 2/2005 | Drobnik et al. | 250/506.1 |
| 2006/0063962 A1 * | 3/2006 | Drobnik et al. | 600/7 |
| 2009/0131735 A1 * | 5/2009 | Drobnik et al. | 600/8 |
| 2010/0200778 A1 * | 8/2010 | Drobnik et al. | 250/506.1 |
| 2010/0268015 A1 * | 10/2010 | Drobnik et al. | 600/7 |

* cited by examiner

*Primary Examiner* — Christine H Matthews
*Assistant Examiner* — Sunita Reddy
(74) *Attorney, Agent, or Firm* — Knobbe, Martens, Olson & Bear LLP

(57) ABSTRACT

A device for loading and customizing brachytherapy carriers based on the principles of optimizing a more precise and predictable dosimetry, and adaptable to the geometric challenges of a tumor bed in a real-time setting. The present invention relates to a specialized loading device designed to enable a medical team to create a radionuclide carrier for each patient and tumor reliably, reproducibly and efficiently.

14 Claims, 6 Drawing Sheets

APPARATUS FOR LOADING DOSIMETRICALLY CUSTOMIZABLE BRACHYTHERAPY CARRIERS

BACKGROUND OF THE INVENTION

1. Field of the Invention

The invention generally relates to highly adaptable specialized loaders for loading a broad range of brachytherapy carriers, and more specifically to loaders oriented for precisely and predictably loading specialized tile and gore radionuclide carriers that are highly adaptable in real-time in order to treat diverse tumors typically not well treated with current methodologies.

2. Background Information

Tumors in living organisms are highly variable in size, location and their amount of infiltration into normal tissues, the variability of tumors in general make them very difficult to treat with a one-size fits all approach. Furthermore, the extent of tumors and/or void upon debulking are typically not known until presented in the operating room. Thus the options necessary to effectively treat a tumor or tumor bed need to be quite diverse.

Brachytherapy involves placing a radiation source either into or immediately adjacent to a tumor. It provides an effective treatment of cancers of many body sites. Brachytherapy, as a component of multimodality cancer care, provides cost-effective treatment. Brachytherapy may be intracavitary, as in gynecologic malignancies; intraluminal, as in but not limited to esophageal or lung cancers; external surface, as in but not limited to cancers of the skin, or interstitial, as in but not limited to the treatment of various central nervous system tumors as well as extracranial tumors of the head and neck, lung, soft tissue, gynecologic sites, rectum, liver, prostate, penis and skin.

The currently available brachytherapy devices and techniques are lacking in the following areas: 1) the current carriers are unable to easily accommodate anatomically conformal and reproducible brachytherapy doses; 2) do not facilitate real-time dosimetric customization for sparing normal tissue, while delivering effective and safe doses of radiation to tumors; and 3) are not able to incorporate additional therapeutic agents, including chemotherapy, and viral, targeted, and DNA damage repair inhibitors The present invention addresses the deficiencies associated with current brachytherapy devices for treating highly variable tumors and comprises of novel brachytherapy radioisotope carrier loading systems for providing real-time customized brachytherapy treatment to patients with tumors difficult to control using conventional radiation therapy techniques.

SUMMARY OF THE INVENTION

The present invention generally relates to devices and methods for loading a preformed radionuclide carrier in a patient to help cure, slow progression or regrowth, or ameliorate symptoms associated with tumors. And more specifically to a versatile dosimetrically customizable brachytherapy real-time loading system for loading a carrier with a targeted radionuclide dose to specific tissues on or within the human body.

Embodiments of the present invention relate to a specialized loading device designed to enable a medical team to create a radionuclide carrier for each patient and tumor reliably, reproducibly and efficiently.

An embodiment of the present invention includes a device for loading preformed brachytherapy carriers comprising a base with a loading bed, a lid with a loading bed insert, one or more entry loading channels paired with an equal number of exit loading channels; and a loading channel support structure. Preferable embodiments include having the one or more entry loading channels and a loading channel support structure in the base; and the one or more exit loading channels in the lid. Additional embodiments allow for the number of entry and exit loading channel pairs to be from 1, 2, 3, 4 or 5, with 1, 2 or 3 most preferred.

Another embodiment of the present invention includes a device for loading brachytherapy carriers comprising a base and a lid; and wherein the base of a loader functions to guide an initial path of a loading needle for seed placement in a soft carrier; provides dimensional stability to a soft carrier during the loading process; centers the soft carrier left to right within the base during the loading process; and shields the user from excess radiation exposure; additionally, the lid of the loader nests and/or mates with the base to become a fully closed and unit; and the loader functions to guide the final path of the loading needle, entirely through the carrier; provides dimensional stability to the soft carrier during the loading process; maintains the position of the carrier superior-inferiorly within the base during the loading process; positions the carrier front to back within the base during the loading process; and shields the user from excess radiation exposure.

An additional embodiment includes various numbers of paths for passing the needles used to load the carriers. There may be one, two, three, four or five paths for loading needles which extend from a proximal surface of a base, through an interior cavity of the loading device and exits through a distal surface of the lid. 1-3 paths is preferred and 1-2 paths most preferred.

Additional embodiments include an interior cavity formed when the lid is properly placed on the base that is substantially filled when a carrier is placed within the cavity and may be of a fixed dimension specific to the loader which may be selected from any one of; 1×2 cm, 2×2 cm or 3×2 cm; 1×3 cm, 2×3 cm or 3×3 cm 1×4 cm, 2×4 cm or 3×4 cm. Additional ½ cm or ¼ cm dimensions within the above dimensions are also contemplated.

Further embodiments of the present invention include the entry path of the loading needle that is an equal distance from a bottom surface of the loader the exit path of the loading needle is from a bottom surface of the loader. And wherein the entry path is in a horizontal plane with the final path. Additionally, the entry and exit loading paths/channels may be between 1-8 mm from the bottom surface of the loading device, with 1-5 mm preferred, depending on the materials used to construct the loader.

Further embodiments include the ability to change the dimensions of the interior cavity by including loading bed liners or a shortened lid with a tooth feature. The bed liners contemplated are of a specific size to fit within the loading bed and have a specific width to raise a carrier to be loaded in relation to the entry and exit loading channels. One or more bed liners may be used and they may have a preferred thickness of 1 mm.

An embodied tooth feature can be formed for embodiments in which the distal end of the lid is shorter than a distal end of the base. A loading bed tooth is used to mate the distal end of a shortened lid with the loading bed of the base. The tooth contains the one or more exit loading channels; and thus shortens the distance between the entry loading channel and the exit loading channel as compared to a full-length lid which ends adjacent to the distal end of the base. The tooth placement on a lid is selected by the user to provide structural support to a carrier that is shorter than the length of the loader bed.

Still further embodiments of the present invention utilize the positioning of the entry and exit path channels in relation to the loader bed to determine and customize and provide a radionuclide carrier with a precise and predictable dosimetry.

Further uses of the presently embodied include using the loader for loading preformed carriers, either to create pre-packaged hot carriers or to load "cold" carriers just prior to use.

Additional embodiments may include shielding of the base and/or lid, sterilizable single use loaders or multi-use loaders for manual or automated loading and wherein the loader is loaded in real-time with one or more radioactive seeds.

Further additional embodiments include real-time visual assistance embodiments such as stamping of tile dimensions in large letters on loader top, color coordination of loader in relation to tile sizes, isotopes used, and seed depths.

Yet further embodiments may include the addition of a locking mechanism for a loader in order to maintain the lid in a closed position until the user purposely disengages the locking mechanisms.

Still further embodiments may include the addition enhanced gripping or texture features for a loader in order to assist with handling a loader in a real-time operating field setting.

A further embodiment includes a device for loading brachytherapy carriers including a base and a lid; and wherein the base of the loader functions to guide an initial path of a loading needle for seed placement in a soft carrier; provides dimensional stability to a soft carrier during the loading process; centers the soft carrier left to right within the base during the loading process; and shields the user from excess radiation exposure. In this embodiment the lid of the loader nests and/or mates with the base to become a fully closed unit; and the loader additionally functions to guide the final path of the loading needle, entirely through the carrier; provides dimensional stability to the soft carrier during the loading process; maintains the position of the carrier superior-inferiorly within the base during the loading process; positions the carrier front to back within the base during the loading process; and shields the user from excess radiation exposure. Additionally, the base has, two initial paths for loading needles which extend from a proximal surface of a base, through an interior cavity of the loading device and exits through a distal surface of the lid; an interior cavity is formed when the lid is properly placed on the base and the interior cavity is substantially filled when a carrier is placed within the cavity. The interior cavity may be a fixed dimension specific to the loader for example, having 2×4 cm interior cavity.

Another embodied device for loading brachytherapy carriers includes a base and a lid. The base of the loader functions to guide an initial path of a loading needle for seed placement in a soft carrier; provides dimensional stability to a soft carrier during the loading process; centers the soft carrier left to right within the base during the loading process; and shields the user from excess radiation exposure. The lid of the loader nests and/or mates with the base to become a fully closed unit; and the loader additionally functions to guide the final path of the loading needle, entirely through the carrier; provides dimensional stability to the soft carrier during the loading process; maintains the position of the carrier superior-inferiorly within the base during the loading process; positions the carrier front to back within the base during the loading process; and shields the user from excess radiation exposure. Additionally in a contemplated embodiment the base has, two initial paths for loading needles which extend from a proximal surface of a base, through an interior cavity of the loading device and exits through a distal surface of the lid. An interior cavity is formed when the lid is properly placed on the base and the interior cavity is substantially filled when a carrier is placed within the cavity. The interior cavity is of a fixed dimension specific to the loader and the dimensions of the interior cavity may be decreased in depth by the addition of one or more bed liners within the loading bed; and/or may be decreased in width by the utilization of a shortened lid with a tooth feature.

BRIEF DESCRIPTION OF THE DRAWINGS

The principles of the present invention will be apparent with reference to the following drawings, in which like reference numerals denote like components.

DETAILED DESCRIPTION OF THE INVENTION

Definitions

For the purposes of the present invention Brachytherapy is defined as radiation treatment in which the source of the radiation is placed close to the surface of the body or within the body or a body cavity a short distance from the area being treated.

For the purposes of the present invention Teletherapy is defined as radiation treatment in which the source of the radiation is at a distance from the body.

For the purposes of the present invention High Dose Rate is considered to be defined as the treatment with radiation doses above 12,000 cGy/hr.

For the purposes of the present invention Low Dose Rate is considered to be defined as the treatment with radiation in the dose range of 400-2000 cGy/hr For the purposes of the present invention High Z Materials are considered to be defined as any element with an atomic number greater than 20, or an alloy containing such materials.

For the purposes of the present invention the term Hot is considered to be a material that is Radioactive and the term Cold is considered to mean a material is low in radioactivity; or not radioactive.

For the purposes of the present invention Dosimetry is defined as the process of measurement and quantitative description of the radiation absorbed dose (rad) in a tissue or organ.

For the purposes of the present invention a Tile Carrier sometimes also referred to as a GammaTile is defined as a type of radionuclide carrier that is planar and maintains a two-dimensional planar geometry when placed in use to treat tumors.

For the purposes of the present invention a Gore Carrier sometimes also referred to as a GammaGore is defined as a type of radionuclide carrier that, while initially planar, will when placed into an operative cavity or similar space assume a 3-dimensional shape and conform to the treatment environment while maintaining the geometry necessary for an effective implant.

For the purposes of the present invention the term Tumor: is defined as an abnormal growth of tissue resulting from uncontrolled, progressive multiplication of cells; which can be benign or malignant.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Carrier Systems

Figure 6:
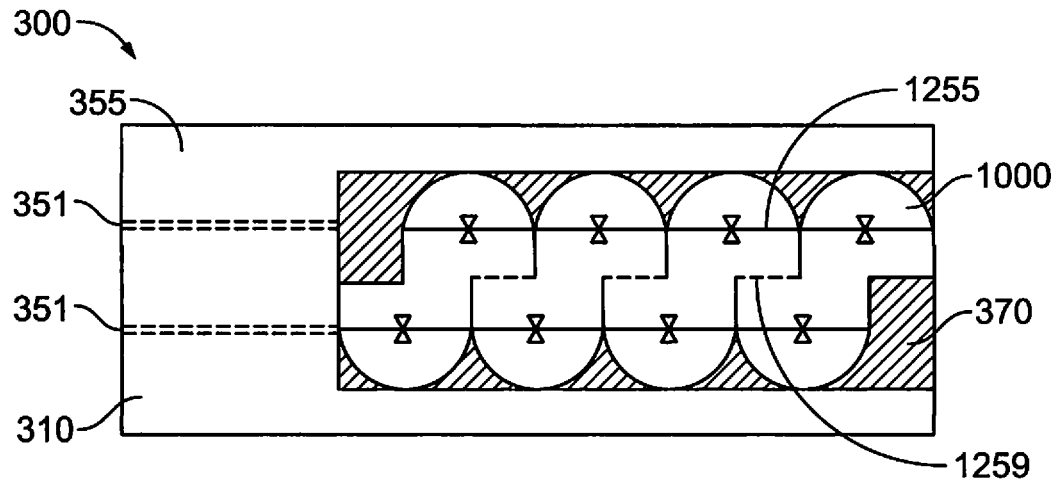
FIG. 6 is a top plan view of another embodied loading device with a gore carrier.
Figure 7:
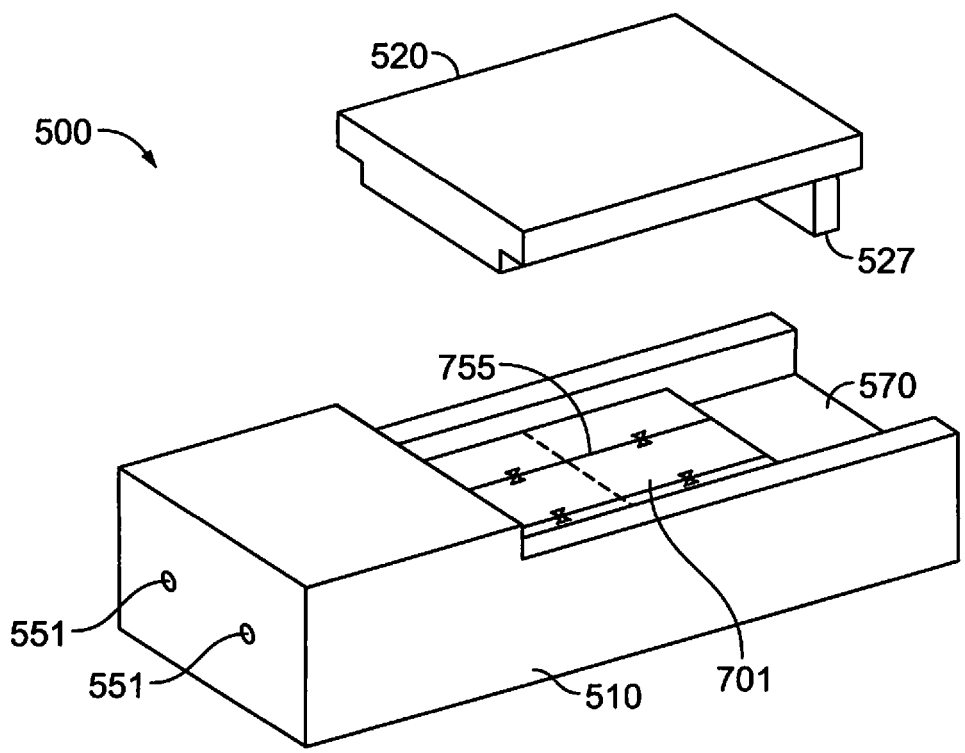
FIG. 7 shows a perspective view of the base of an embodied loading device with a tile carrier in the loading bed and an enhanced lid.

Generally the carrier systems described herein and exemplified in FIGS. 6-7 involve the utilization of small individual implantable carriers in the form of gores (as shown in FIG. 6) and tiles (as shown in FIGS. 7) which are designed to be bearers of therapeutic agents such as radioactive seeds to produce a dosimetrically customizable implant in real time for each patient and tumor.

The carrier systems are designed to create a carrier which allows for more precise and predictable dosimetry; an improved geometry with a better orientation of seeds to one another especially in the settings of real-time, intraoperative environments; is fully customizable to adjust to size/volume, location, and tumor type; and can provide differential dosing of tumor/tumor bed vs. normal tissues.

Loading Devices

The present invention includes a specialized loading device designed to enable the medical team to create a radionuclide carrier for each patient and tumor reliably, reproducibly and efficiently.

FIGS. 1-8 demonstrate the use of a specialized loader system for loading specialized carriers with radioactive seeds. The loaders of the present invention may be used with the carriers either to create prepackaged hot carriers or to load "cold" carriers just prior to use.

The embodied loaders can be single or multi-use, sterilizable, and shielded if desired. They are designed to load either standard or high-Z material carriers in an accurate, efficient, and real-time manner. The loaders are of similar designs, dimensionally specific, and each consists of two components, the base and the lid.

The loader designs of the present invention can be made to accommodate a wide variety of GammaTile and GammaGore dimensions and styles. They are illustrated to accommodate seed-in-suture, but can be easily adapted for loose seeds or other configurations.

When loading a seed in suture a needle longer than the loader is used and pulled through the loader channel holes on the proximal end of the base and the distal of the lid. Once the needle protrudes it is pulled the rest of the way with clamps or a needle-nose plier. One example is wherein you have a 60 mm loader you would want to use a 70 mm needle to feed through the loader channels and deposit the seeds within the carrier.

The Gamma Tile Loader System

The Gamma Tile loader (GT-loader) is conceived as a sterilizable single or multi-use device for manual or automated loading (in real time or for pre-loading) of carriers such as but not limited to GammaTiles (GT) or GammaGores (GG) with radioactive seeds such as $I^{125}$, $Cs^{131}$ or $Pd^{111}$ or other materials. The loaders may be constructed of metal, plastic or composite material, and manufactured by casting, molding, stamping, forming or 3D printing. Embodiments of the loaders contemplated may include shielding either by way of construction with a high Z material, or with other materials with a sufficient dimension (thickness) to provide the necessary dose attenuation for a user.

Alternative embodiments may remain unshielded, and be made of materials suitable for the purpose including but not limited to tungsten, stainless steel, nylon or plastic.

The embodied Loader device generally has two components, a base and a lid. But each component has multiple and specialized functions when used to load radionuclide carriers.

The Base

The base has a "bed" or a space into which a preformed radionuclide or brachytherapy carrier (GT or GG) is placed. This bed area is of a fixed dimension specific to the loader, and loaders are contemplated in multiple sizes identified for this purpose by the bed size. Bed sizes contemplated may be almost any dimension that falls between 1 cm×1 cm and 4 cm×4 cm (for example 1×2 cm, 2×3 cm and 3×4 cm).

The base of the loaders function to: 1) guide the initial path of the loading needle for seed placement in the carrier; 2) provide dimensional stability to the soft carrier during the loading process; 3) center the carrier left-right within the base during the loading process; and 4) shield the user.

The "structure" of the base consists of a portion with an internal tunnel of appropriate length and diameter (e.g. 20 mm×1.2 mm) which guides the initial path of the loading needle for accurate seed placement in the carrier; and 2) sufficient material to constrain the carrier in the bed on 4 sides with; 3) exterior dimensions which may vary with the material/construction materials used; and 4) the need for a shielded or unshielded device.

Figure 1:
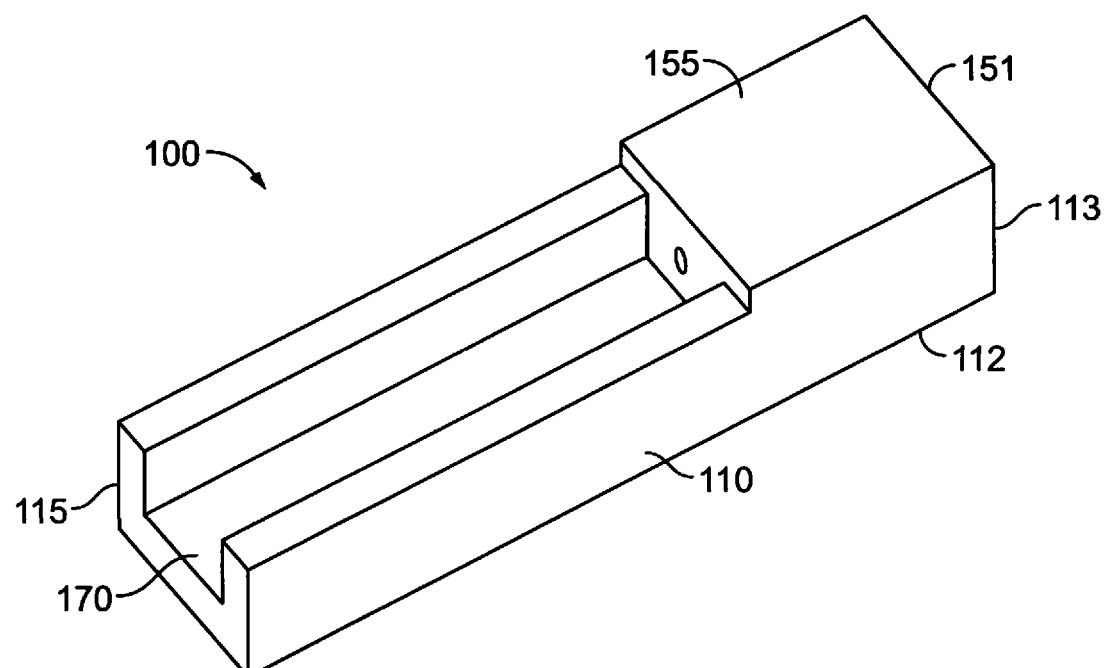
FIG. 1 shows a perspective view of the base of an embodied loading device.

An exemplary base of a loader device 100 is shown in FIG. 1, the base 110 has a bottom surface 112 a top surface 114, a proximal end 113, a distal end 115. A radionuclide loading entry channel 151 is located on the proximal end 113 of the base 110 and a loading support channel 155 begins at the loading entry channel 151 and extends through the base 110 until reaching the loading bed 170. The loading bed 170 extends from the end of the support channel 155 until the distal end 115 of the base 110.

The Lid

The lid of a contemplated loader functions to: 1) guide the final path of the loading needle, entirely through the carrier; 2) provide dimensional stability to the soft carrier during the loading process; 3) position the carrier superior-inferiorly within the base during the loading process; 4) position the carrier front to back within the base during the loading process; and 5) shield the user.

An additional aspect of the lid is its function as a guide for the terminal path of the loading needle through the specific placement of an opening along its far aspect to accept the tip of the loading needle and thereby assure accurate placement of the seeds. Lids is conceived of as being made of as a set for each standard base so that, as an example, a 1×4 cm base can be used to load a 1×2 cm, 1×3 cm, or 1×4 cm carrier by utilizing a lid of appropriate length.

A further feature of this design is that there is a "tooth" on the end of the less than full length lids which add further stability when loading shorter length carriers.

Figure 2:
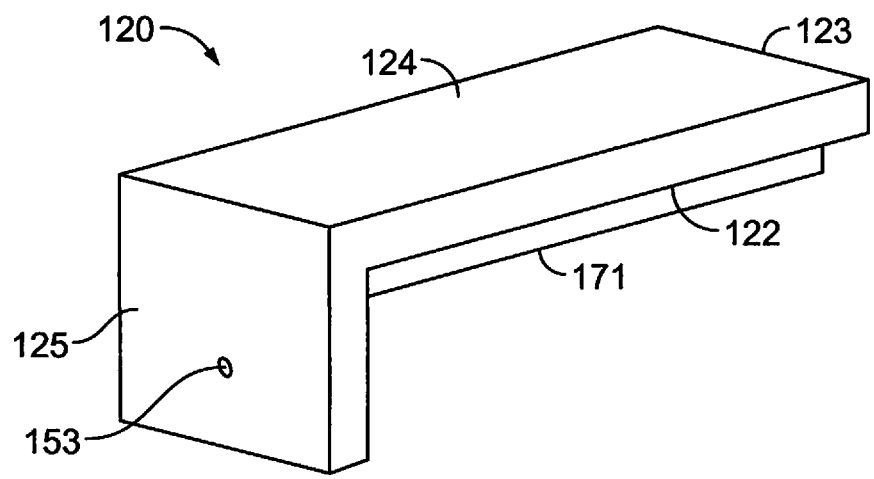
FIG. 2 shows a perspective view of a lid of an embodied loading device which would fit with the base of FIG. 1.

An exemplary lid of a loader device 100 is shown in FIG. 2, the lid 120 has a bottom surface 122 a top surface 124, a proximal end 123, a distal end 125. A radionuclide loading exit channel 153 is located on the distal end 125 of the lid 120. A loading bed insert 171 is located on the bottom surface 122 of the lid 120 and is configured to have dimensions that mate with the loading bed 170 of the base.

Figure 3:
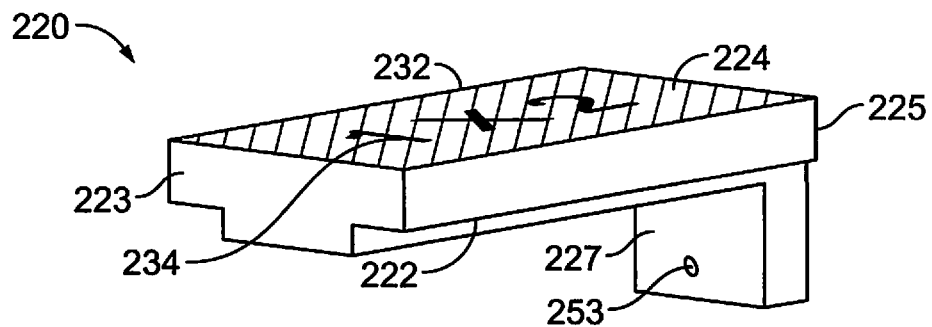
FIG. 3 shows an alternative shorter lid with enhanced properties and a tooth mechanism that would also mate with the lid of FIG. 1.

FIG. 3 illustrates another embodied lid 220 with a bottom surface 222 a top surface224 which has real time visual enhancement features 234 to help assist the user in the operating field to determine the correct properties of the loader being used. In this case the visual enhancement features are stamped dimensions 234. The top surface 224 also has an external texture feature 232 which assists the user with handling the loader 200 in an operating field setting. In applications where the distance from the proximal end 223, to the distal end 225 of a lid 220 is less than the length of the loading bed 170 the lid 220 is designed to mate with the loading bed 270 so a tooth feature 227 is present on the distal end 225 of the lid 220. The tooth 227 mates with the loading bed 270 at a dosimetrically advantageous place in order to create a smaller loading cavity and provide structural support for a shorter radionuclide carrier. The exit channel 253 extends through the tooth 227 and out of the device 200.

Figure 4A:
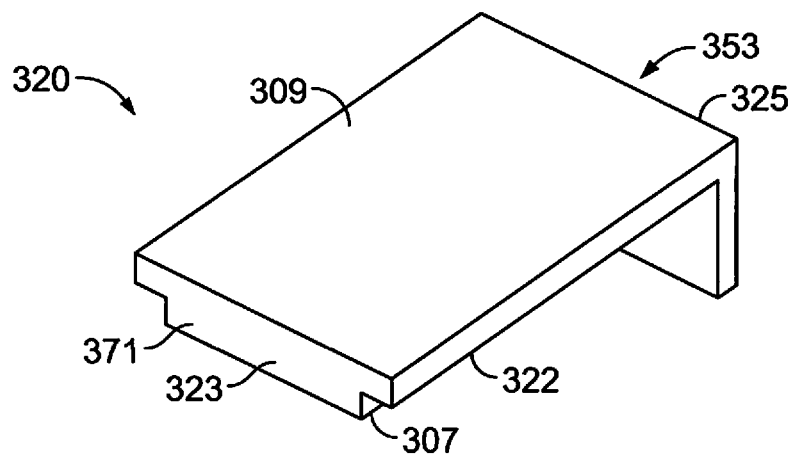
FIG. 4 comprises of perspective views of FIG. 4A which shows a lid, FIG. 4B which shows a base, and FIG. 4C which shows the base and lid together as an embodied loading device.
Figure 4B:
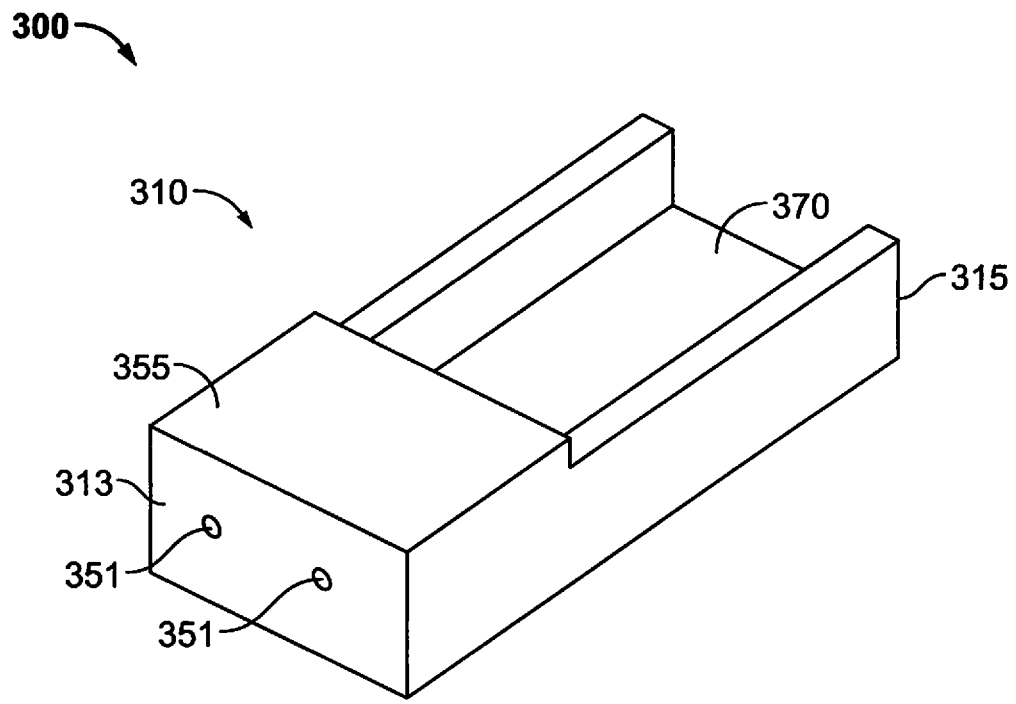
Figure 4C:
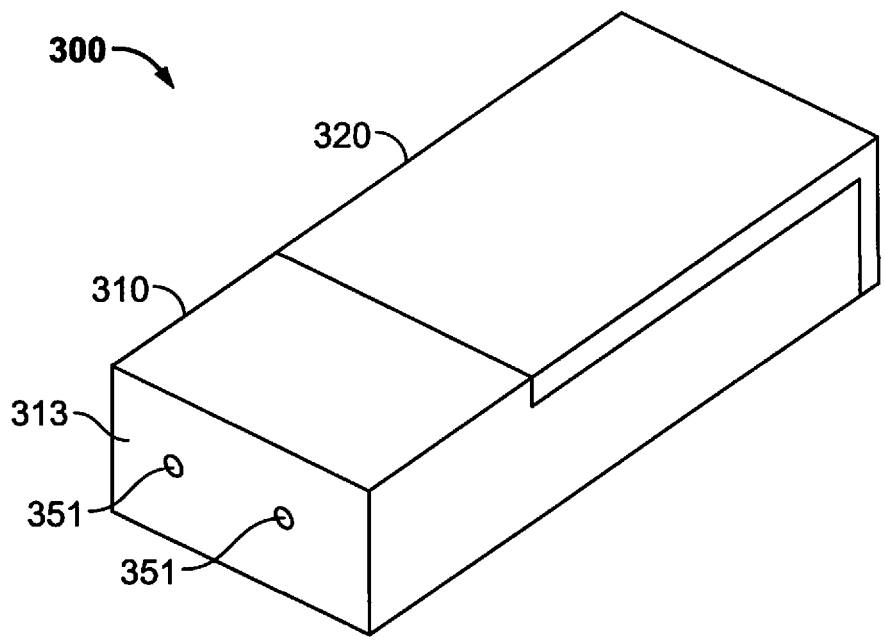

FIG. 4 includes FIGS. 4A, 4B and 4C wherein FIG. 4A shows a perspective view of a lid 320 to an embodied loading device 300; FIG. 4B shows a perspective view of the base 310 of an embodied loading device 300; and FIG. 4C shows a perspective view of an embodied loading device 300 with the lid 320 in its secured position on the base 310. The lid 320 has a bottom surface 322 and a top surface 324 a proximal end 323 and a distal end 325 and a loading bed insert 371 located on the bottom surface 322 and running from the proximal end 323 to the distal end 325. Additionally there are loading channel 353 exit holes (not shown) extending through the distal end 325 of the lid. The base 310 as shown in FIG. 4B comprises of the proximal end 313 and a distal end 315 a proximal end loading channel 351 and a loading channel support structure 355 which provides enough depth to guide a needle in a consistent and accurate pathway as the needle tip travels through any loading material if present, and exits out a loading channel exit hole 353. Additionally the loader 300 comprises a loading bed 370 in which appropriately sized carrier material is placed to be loaded. Once a carrier is placed into the loading bed 370 to be loaded the lid 320 is placed onto the base 310, as shown in FIG. 4C, such that the loading bed insert 371 located on the bottom surface 322 of the lid 320 engages with the loading bed 370 portion of the base 310 the depth of the loading bed insert 371 is chosen so that it is deep enough to sandwich the carrier material in place during the process of loading but not too much depth which crushes the carrier and repulses the ability of the loading needle to extend through a loading channel 351.

Figure 5:
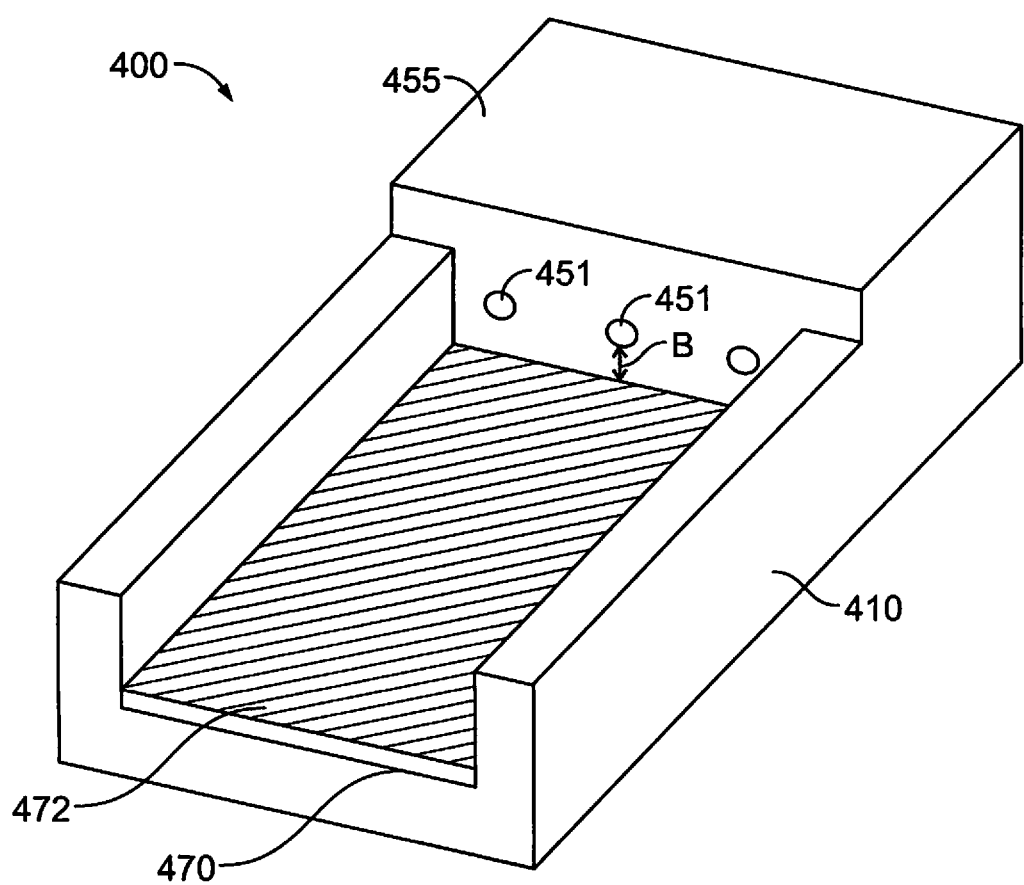
FIG. 5 is a perspective view of an alternative loader base.

Another loading device which allows for variable customization is shown in FIG. 5. The loader shown in this embodiment displays the variable distance possibilities between the loader bed 470 and the loading entry channels 451 and is measured as distance "b". This "b-value" can be made shorter by adding one or more bed-liners 472 placed into the bed 470 of the loader 400. The bed liners can be as thin as 0.5 mm and as wide as 2.0 mm, with 0.75 to 1.5 mm preferred and 1 mm most preferred. This "b"-value variation can be used to provide various loading arrangements which allows the user to create a carrier with customized but variable depths of carrier material and allows for more precise and predictable real-time dosimetry in the operating field.

FIG. 6 is a top plan view of an embodied gore carrier 1000 shown when placed in the loading bed 370 of loader device 300. FIG. 6 shows the gore 1000 placed within the loading bed 370 portion of the loader 300. The lid 320 portion of the loader has been removed so that the gore 1000 is visible and one can see that the orientation lines 1255 of the gore 1000 align directly with the loading channel support structure 355 such that when a needle loader enters through the proximal end loading channel 351 and extends through the loading channel support structure 355 and enters into the loading bed portion 370 of the base 310 where a carrier gore 1000 is in a secured position the loading needle enters into the predetermined placement on the gore 1000 based on dosimetry needs for treatment. Once the gore 1000 is loaded it may be trimmed along the trim lines 1259 present on the antipodal surface of the gore 1000 if necessary.

FIG. 7 is a perspective view of a tile carrier 601 when placed in the loading bed 570 of the loading device 500. The lid 520 portion of the loader has been removed so that the tile 701 is visible and one can see that the orientation lines 755 of the tile 701 align directly with the proximal end loading channel 551 such that when a needle loader enters through the proximal end loading channel 551 and extends through the loading channel support structure 555 and enters into the loading bed portion 570 of the base 510 when a carrier tile 701 is in a secured position the loading needle enters into the predetermined placement on the tile 701 based on dosimetry needs for treatment. Additionally, with the lid 520 removed one can see that the tile carrier 701 does not extend the full distance to the end of the loader bed 570. In these cases a specialized lid 520 with a tooth portion 527 can mate with the loader bed 570 and the tooth portion 527 proximity to the shortened tile 701 provides structural support and allows the tile to be more accurately loaded.

Figure 8:
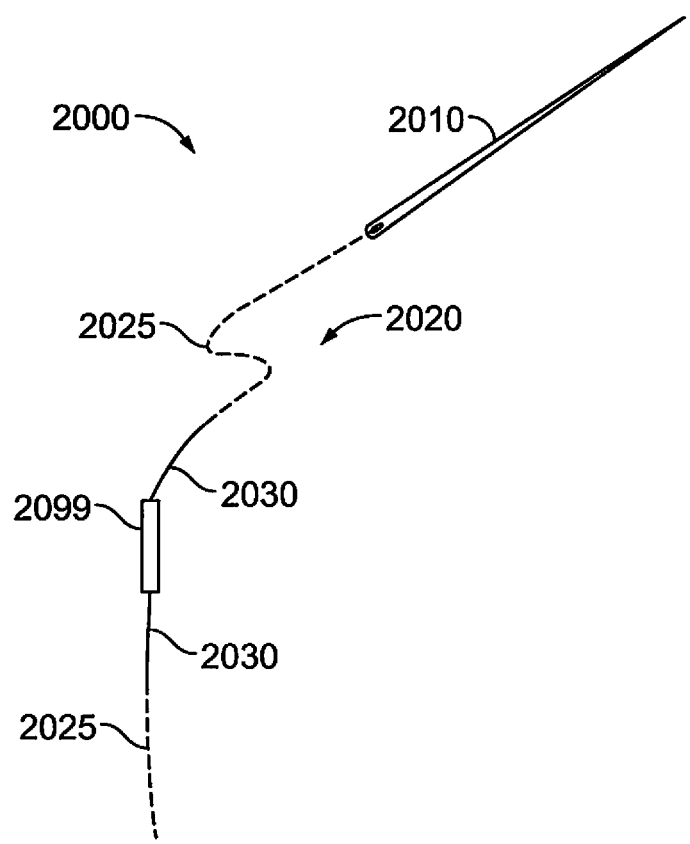
FIG. 8 shows a plan view of an embodied needle radionuclide seed loading device.

When a needle loading apparatus is used to load the radioactive seeds into the carriers such as that described in FIG. 8, the needle apparatus 2000 feeds through the proximal end loading channel 151 and extends through the loading channel support structure 155 and enters into the loading bed portion 170 of the base 110 where a carrier tile such as 601(not shown) is in a secured position. The needle apparatus 2000 feeds through the tile carrier 601 and exits out the loading channel exit hole 353. Once the tip of the needle 2010 of the needle apparatus extends through the exit hole 353 the needle 2010 is grasped with a needle-puller and pulled through until the thread 2020 provides a visual determination that the carrier is loaded properly and the seeds are in their proper location. When the seed is placed at the proper depth all of the offset color 2030 (such as purple) disappears inside of the tile 601 and the loader device and the regular color thread 2025 is trimmed away.

Although the invention has been described with reference to the above example, it will be understood that modifications and variations are encompassed within the spirit and scope of the invention. Accordingly, the invention is limited only by the following claims.

What is claimed is:

1. A loading device comprising:
   a base including:
   a loading bed having an opening opposite a bottom surface and between opposing side walls extending upward from the bottom surface, the loading bed sized to receive a radionuclide carrier therein; and a first loading channel support structure adjacent one end of the loading bed and including an entry channel through a central portion of the loading channel support structure such that the entry channel receives a needle and guides the needle through the loading channel support structure into and through the loading bed without the needle contacting the bottom surface or side walls of the loading bed; and, a lid that engages with the base such that the base and the lid enclose a radionuclide carrier on the loading bed, the lid including:

a top surface sized to cover the opening of the loading bed;

a loading bed insert that engages internal surfaces of the side walls of the loading bed; and a second loading channel support structure at an end of the lid such that the first and second loading channel support structures are at opposite ends of the loading device when the base and lid are engaged, the second loading channel support structure including an exit channel through a central portion of the second loading channel support structure, such that the exit channel receives the needle after passing through the entry channel of the base and the radionuclide carrier positioned on the loading bed in order to guide the needle out of the loading device.

2. The loading device of claim 1, wherein the loading bed insert is sized to engage the radionuclide carrier positioned on the loading bed.

3. The loading device of claim 1, wherein the entry channel is positioned such that the needle maintains a distance of more than 1 mm from the bottom surface of the base.

4. The loading device of claim 1, wherein an interior cavity formed between the base and the lid has dimensions of about 1-3 mm by 1-4 mm.

5. The loading device of claim 1, wherein the first loading channel support structure further comprises a second entry channel positioned to receive the needle and the second loading channel support structure further comprises a second exit channel positioned to receive the needle after passing through the second entry channel.

6. The loading device of claim 5, wherein the first loading channel support structure further comprises a third entry channel positioned to receive the needle and the second loading channel support structure further comprises a third exit channel positioned to receive the needle after passing through the third entry channel.

7. The loading device of claim 1, further comprising one or more bed liners sized to fit within the loading bed and to raise the radionuclide carrier above the bottom surface of the loading bed.

8. The loading device of claim 7, wherein a first bed liner has a thickness of about 1 mm.

9. The loading device of claim 1, further comprising one or more bed liners positioned within the loading bed in order to decrease a distance between the loading bed and the loading bed insert to secure the radionuclide carrier between the loading bed and the loading bed insert.

10. The loading device of claim 1, further comprising a locking mechanism configured to maintain the lid in a closed position until a user purposely disengages the locking mechanism.

11. A method of loading a carrier with a radioactive seed, the method comprising:

providing a base including:

a loading bed formed by a bottom surface and opposing side walls extending upward from the bottom surface such that the loading bed receives a carrier therein, the carrier configured to receive a radioactive seed; and an entry channel positioned to receive a needle configured to position the radioactive seed into the carrier;

positioning the carrier on the loading bed;

placing a bed liner on the loading bed prior to positioning the carrier on the loading bed, the bed liner having a thickness of at least 1 mm;

engaging a lid with the base, the lid comprising a loading bed insert sized to engage the opposing side walls of the loading bed, in order to form an interior cavity enclosing the carrier, the lid comprising an exit channel that receives the needle after passing through the entry channel of the base and the carrier positioned within the interior cavity;

inserting the needle coupled to the radioactive seed into the entry channel; and pushing the needle into the interior cavity, through the carrier and at least partially out of the interior cavity through the exit channel so that the radioactive seed is secured within the carrier positioned within the interior cavity.

12. The method of claim 11, further comprising:

removing the lid from the base in order to expose the carrier loaded with the radioactive seed on the loading bed; and removing the carrier from the loading bed.

13. The method of claim 11, wherein the entry channel and exit channel are coaxial.

14. The method of claim 11, wherein the needle is coupled to the radioactive seed by a thread that is connected to both the needle and the radioactive seed.

\* \* \* \* \*